United States Patent
Lange (10) Patent No.: US 11,000,235 B2
(45) Date of Patent: May 11, 2021

(54) MONITORING PROCEDURE FOR EARLY WARNING OF CARDIAC EPISODES

(71) Applicant: ChroniSense Medical Ltd., Yokneam (IL)

(72) Inventor: Daniel H. Lange, Kfar Vradim (IL)

(73) Assignee: ChroniSense Medical Ltd., Yokneam (IL)

(*) Notice: Subject to any disclaimer, the term of this patent is extended or adjusted under 35 U.S.C. 154(b) by 0 days.

(21) Appl. No.: 15/069,739

(22) Filed: Mar. 14, 2016

(65) Prior Publication Data
US 2017/0258406 A1 Sep. 14, 2017

(51) Int. Cl.
| | | |
|---|---|---|
| A61B 5/00 | (2006.01) | |
| A61B 5/0452 | (2006.01) | |
| A61B 5/04 | (2006.01) | |
| A61B 5/316 | (2021.01) | |
| A61B 5/341 | (2021.01) | |
| A61B 5/349 | (2021.01) | |

(52) U.S. Cl.
CPC ............ *A61B 5/7246* (2013.01); *A61B 5/316* (2021.01); *A61B 5/341* (2021.01); *A61B 5/349* (2021.01); *A61B 5/681* (2013.01); *A61B 5/7275* (2013.01)

(58) Field of Classification Search
None
See application file for complete search history.

(56) References Cited

U.S. PATENT DOCUMENTS

| 3,885,552 A | 5/1975 | Kennedy |
| 3,898,984 A | 8/1975 | Mandel et al. |
| 4,331,154 A | 5/1982 | Broadwater et al. |
| (Continued) | | |

FOREIGN PATENT DOCUMENTS

| CN | 1335756 A | 2/2002 |
| CN | 106901747 A | 6/2017 |
| (Continued) | | |

OTHER PUBLICATIONS

"International Search Report" and "Written Opinion of the International Searching Authority," Patent Cooperation Treaty Application No. PCT/IL2017/050242, dated Jun. 13, 2017, 12 pages.

(Continued)

*Primary Examiner* — Michael W Kahelin
*Assistant Examiner* — Elizabeth K So
(74) *Attorney, Agent, or Firm* — Carr & Ferrell LLP (57) ABSTRACT

Provided are methods and systems for monitoring cardiac function. A series of heartbeat waveforms is collected during a pre-determined time period. The series is collected either from an individual or a plurality of individuals. A heartbeat waveform space is generated based on the series of heartbeat waveforms. A test heartbeat waveform is projected onto the heartbeat waveform space. The projected heartbeat waveform is subtracted from the test heartbeat waveform to obtain a pathology descriptive deflections (PDD) vector. A score is calculated based on the PDD vector. Based on the score, a clinical indication associated with at least one disease is provided. The clinical indication includes a warning message regarding an upcoming cardiac episode or a measure of progression or regression of at least one cardiac pathology.

21 Claims, 7 Drawing Sheets

(56) References Cited

U.S. PATENT DOCUMENTS

| | | |
|---|---|---|
| 4,732,158 A | 3/1988 | Sadeh |
| 4,802,486 A | 2/1989 | Goodman et al. |
| 5,050,612 A | 9/1991 | Matsumura |
| 5,316,008 A | 5/1994 | Suga et al. |
| 5,503,148 A | 4/1996 | Pologe et al. |
| 5,692,505 A | 12/1997 | Fouts |
| 6,047,203 A | 4/2000 | Sackner et al. |
| 6,139,494 A | 10/2000 | Cairnes |
| 6,527,725 B1 | 3/2003 | Inukai et al. |
| 7,184,809 B1 | 2/2007 | Sterling et al. |
| 7,479,111 B2 | 1/2009 | Zhang et al. |
| 7,544,168 B2 | 6/2009 | Nitzan |
| 7,738,935 B1 | 6/2010 | Turcott |
| 8,172,764 B2 | 5/2012 | Gregson et al. |
| 8,602,997 B2 | 12/2013 | Banet et al. |
| 8,866,606 B1 | 10/2014 | Will et al. |
| 10,470,692 B2 | 11/2019 | Lange et al. |
| 10,687,742 B2 | 6/2020 | Lange et al. |
| 2001/0005773 A1 | 6/2001 | Larsen et al. |
| 2001/0029326 A1 | 10/2001 | Diab et al. |
| 2002/0095077 A1 | 7/2002 | Swedlow et al. |
| 2002/0133068 A1 | 9/2002 | Huiku |
| 2003/0009091 A1 | 1/2003 | Edgar, Jr. et al. |
| 2003/0036685 A1 | 2/2003 | Goodman |
| 2003/0065269 A1 | 4/2003 | Vetter et al. |
| 2003/0109776 A1 | 6/2003 | Jacques |
| 2003/0163033 A1 | 8/2003 | Dekker |
| 2004/0215095 A1 | 10/2004 | Lee et al. |
| 2005/0070775 A1 | 3/2005 | Chin et al. |
| 2005/0215913 A1 | 9/2005 | Lee et al. |
| 2005/0281439 A1 | 12/2005 | Lange |
| 2006/0074322 A1 | 4/2006 | Nitzan |
| 2006/0264767 A1 | 11/2006 | Shennib |
| 2007/0142720 A1 | 6/2007 | Ridder et al. |
| 2007/0191725 A1 | 8/2007 | Nelson |
| 2008/0146954 A1 | 6/2008 | Bojovic et al. |
| 2008/0208069 A1* | 8/2008 | John .................. A61B 5/04012 600/509 |
| 2008/0214961 A1 | 9/2008 | Matsumoto et al. |
| 2008/0221419 A1 | 9/2008 | Furman |
| 2008/0255433 A1 | 10/2008 | Prough et al. |
| 2009/0024011 A1 | 1/2009 | Huiku |
| 2009/0163821 A1 | 6/2009 | Caros et al. |
| 2009/0247848 A1 | 10/2009 | Baker, Jr. |
| 2010/0016694 A1 | 1/2010 | Martin et al. |
| 2010/0179438 A1 | 7/2010 | Heneghan et al. |
| 2010/0192952 A1 | 8/2010 | Melker et al. |
| 2010/0217144 A1* | 8/2010 | Brian .................. A61B 5/0452 600/523 |
| 2010/0298656 A1 | 11/2010 | McCombie et al. |
| 2010/0312079 A1 | 12/2010 | Larsen et al. |
| 2010/0324384 A1 | 12/2010 | Moon et al. |
| 2011/0060200 A1 | 3/2011 | Bernreuter |
| 2011/0066051 A1 | 3/2011 | Moon et al. |
| 2011/0077486 A1 | 3/2011 | Watson et al. |
| 2011/0082355 A1 | 4/2011 | Eisen et al. |
| 2011/0201946 A1 | 8/2011 | Turcott |
| 2011/0224564 A1 | 9/2011 | Moon et al. |
| 2011/0257551 A1 | 10/2011 | Banet et al. |
| 2012/0190944 A1 | 7/2012 | Thaveeprungsriporn et al. |
| 2012/0238834 A1 | 9/2012 | Hornick |
| 2013/0231947 A1* | 9/2013 | Shusterman ........ G06F 19/3418 705/2 |
| 2013/0296665 A1 | 11/2013 | Kassim et al. |
| 2013/0296666 A1 | 11/2013 | Kumar et al. |
| 2013/0296673 A1 | 11/2013 | Thaveeprungsriporn et al. |
| 2013/0310700 A1 | 11/2013 | Wiard et al. |
| 2013/0338460 A1 | 12/2013 | He et al. |
| 2014/0043164 A1 | 2/2014 | Eschelman et al. |
| 2014/0088449 A1 | 3/2014 | Nearing et al. |
| 2014/0142445 A1 | 5/2014 | Banet et al. |
| 2014/0206948 A1 | 7/2014 | Romem |
| 2014/0275888 A1 | 9/2014 | Wegerich et al. |
| 2014/0278229 A1 | 9/2014 | Hong et al. |
| 2015/0109125 A1 | 4/2015 | Kaib et al. |
| 2015/0148622 A1 | 5/2015 | Moyer et al. |
| 2015/0157220 A1 | 6/2015 | Fish et al. |
| 2015/0157262 A1 | 7/2015 | Schuessler |
| 2015/0196257 A1 | 7/2015 | Yousefi et al. |
| 2015/0272510 A1 | 10/2015 | Chin |
| 2015/0305689 A1 | 10/2015 | Gourmelon et al. |
| 2015/0313484 A1 | 11/2015 | Burg et al. |
| 2015/0320328 A1 | 11/2015 | Albert |
| 2015/0342538 A1 | 12/2015 | St. Pierre et al. |
| 2015/0366469 A1 | 12/2015 | Harris et al. |
| 2015/0366518 A1 | 12/2015 | Sampson |
| 2016/0000376 A1 | 1/2016 | Murray et al. |
| 2016/0022220 A1 | 1/2016 | Lee et al. |
| 2016/0089033 A1 | 3/2016 | Saponas et al. |
| 2016/0093205 A1 | 3/2016 | Boyer |
| 2016/0120434 A1 | 5/2016 | Park et al. |
| 2016/0270668 A1 | 9/2016 | Gil |
| 2016/0270677 A1 | 9/2016 | Lin |
| 2016/0360971 A1 | 12/2016 | Gross et al. |
| 2016/0360974 A1 | 12/2016 | Lange |
| 2016/0360986 A1 | 12/2016 | Lange |
| 2016/0361003 A1 | 12/2016 | Lange et al. |
| 2016/0361004 A1 | 12/2016 | Lange et al. |
| 2017/0014037 A1 | 1/2017 | Coppola et al. |
| 2017/0156593 A1 | 6/2017 | Ferber et al. |
| 2017/0202459 A1 | 7/2017 | Cao |
| 2018/0098705 A1 | 4/2018 | Chaturvedi et al. |
| 2018/0132794 A1 | 5/2018 | Lange |
| 2018/0247713 A1 | 8/2018 | Rothman |
| 2019/0015014 A1 | 1/2019 | Lange |

FOREIGN PATENT DOCUMENTS

| | | |
|---|---|---|
| CN | 107920786 A | 4/2018 |
| CN | 107920786 B | 12/2020 |
| EP | 2430975 A1 | 3/2012 |
| EP | 3307146 | 4/2018 |
| EP | 3307150 | 4/2018 |
| EP | 3307162 | 4/2018 |
| EP | 3493734 A1 | 6/2019 |
| EP | 3307146 B1 | 11/2020 |
| WO | WO0047108 A1 | 8/2000 |
| WO | WO2001015597 | 3/2001 |
| WO | WO2006048701 A2 | 5/2006 |
| WO | WO2014022906 A1 | 2/2014 |
| WO | WO2015047015 A1 | 4/2015 |
| WO | WO2015197383 A1 | 12/2015 |
| WO | WO2016110804 A1 | 7/2016 |
| WO | WO2016199121 A1 | 12/2016 |
| WO | WO2016199122 A1 | 12/2016 |
| WO | WO2016199123 A1 | 12/2016 |
| WO | Wo2016199124 A1 | 12/2016 |
| WO | WO2015070030 A1 | 1/2017 |
| WO | WO2017141131 A1 | 8/2017 |
| WO | WO2017158585 A1 | 9/2017 |
| WO | WO2018025257 A1 | 2/2018 |
| WO | WO2018085563 A1 | 5/2018 |
| WO | WO2009130296 A1 | 7/2019 |
| WO | WO2020053858 A1 | 3/2020 |

OTHER PUBLICATIONS

Abtahi, Farhad, "Feasibility of Fetal EEG Recording," Master's Thesis, Department of Signal and System, Chalmers University of Technology, Gothenburg, Sweden, Jan. 1, 2011, 51 pages.

Richardson, Kelly et al., "Electrocardiographic damage scores and cardiovascular mortality," American Heart Journal vol. 149, No. 3, Mar. 1, 2005, pp. 458-463.

Patent Cooperation Treaty Application No. PCT/IL2016/050512, "International Search Report" and "Written Opinion of the International Searching Authority," dated Sep. 18, 2016, 9 pages.

Arza et al., "Pulse Transit Time and Pulse Width as Potential Measure for estimating Beat-to-Beat Systolic and Diastolic Blood Pressure", Computing in Cardiology 2013, pp. 887-890.

Ye et al., "Estimation of Systolic and Diastolic Pressure using the Pulse Transit Time", International Journal of Medical, Health, (56) References Cited

OTHER PUBLICATIONS

Biomedical, Bioengineering and Pharmaceutical Engineering vol. 4. No. 7, 2010, pp. 303-308.
International Search Report and Written Opinion dated Jul. 11, 2016 in Patent Cooperation Treaty Application No. PCT/IL2016/050511 filed May 15, 2016, pp. 1-19.
International Search Report and Written Opinion dated Aug. 18, 2016 in Patent Cooperation Treaty Application No. PCT/IL2016/050514 filed May 15, 2016, pp. 1-20.
International Search Report and Written Opinion dated Aug. 29, 2016 in Patent Cooperation Treaty Application No. PCT/IL2016/050513 filed May 15, 2016, pp. 1-18.
"International Search Report" and "Written Opinion of the International Searching Authority," Patent Cooperation Treaty Application No. PCT/IL2017/050826, dated Oct. 23, 2017, 9 pages.
"Extended European Search Report," European Patent Application No. 16807014.2, dated Oct. 22, 2018, 8 pages.
"Extended European Search Report," European Patent Application No. 16807015.9, dated Jan. 21, 2019, 10 pages.
Gözde, Ateş et al., "Measuring of Oxygen Saturation Using Pulse Oximeter Based on Fuzzy Logic," Medical Measurements and Applications Proceedings (MEMEA), 2012 IEEE International Symposium, May 18, 2012, pp. 1-6.
"Extended European Search Report," European Patent Application No. 16807013.4, dated Jan. 17, 2019, 7 pages.
"International Search Report" and "Written Opinion of the International Searching Authority," Patent Cooperation Treaty Application No. PCT/IL2018/051384, dated Mar. 14, 2019, 15 pages.
"Office Action," European Patent Application No. 16807013.4, dated Aug. 27, 2019, 6 pages.
"International Search Report" and "Written Opinion of the International Searching Authority," Patent Cooperation Treaty Application No. PCT/IL2019/051018, dated Dec. 17, 2019, 14 pages.
"Extended European Search Report," European Patent Application No. 17836517.7, dated Feb. 25, 2020, 5 pages.
"Office Action," Chinese Patent Application No. 201680042023.6, dated Mar. 20, 2020, 10 pages.
"Notice of Allowance," European Patent Application No. 16807013.4, dated May 26, 2020, 7 pages.
"Office Action," European Patent Application No. 16807015.9, dated Aug. 6, 2020, 7 pages.

* cited by examiner

MONITORING PROCEDURE FOR EARLY WARNING OF CARDIAC EPISODES

FIELD

The present application relates to systems and methods for monitoring a person's health status and, more specifically, to systems and methods for prediction and monitoring of cardiac episodes.

BACKGROUND

It should not be assumed that any of the approaches described in this section qualify as prior art merely by virtue of their inclusion in this section.

The first practical electrocardiogram (ECG) was invented over 100 years ago, and its usage basically remains unchanged. The ECG revolutionized the diagnosis and management of cardiac pathology; however, an ECG diagnosis alone is often insufficient as it provides only partial information on cardiac function.

For example, once a myocardial infarction (MI) is detected, an ECG diagnosis is highly specific and effective in localization of the related ischemia. However, when used for screening, ECG diagnostics reveal only about 50% of life threatening MIs in patients admitted with chest pain, which is why biochemical marker analysis, despite being non real-time, is commonly used for a more definitive diagnosis.

Given that coronary artery disease is a main cause of morbidity and mortality in the modern world, and that therapeutic measures are more effective when administered early rather than late, there is a clear need for fast, sensitive, and specific means for early detection of cardiac pathology.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Provided are a system and methods for monitoring cardiac pathology. An example method includes collecting a series of heartbeat waveforms. The method includes generating, based on the series of the heartbeat waveforms, a heartbeat waveform space. The method includes receiving a test heartbeat waveform. The method allows projecting the test heartbeat waveform on the heartbeat waveform space to obtain a projected heartbeat waveform. The method includes subtracting the projected heartbeat waveform from the test heartbeat waveform to obtain a pathology descriptive deflections (PDD) vector. The method allows calculating a score based on the PDD vector. Based on the score, the method includes providing a clinical indication associated with at least one cardiac pathology.

In some embodiments, the series of heartbeat waveforms is collected from an individual. In certain embodiments, the series of heartbeat waveforms is collected from a plurality of healthy individuals. In other embodiments, the series of heartbeat waveforms is collected during a pre-determined time interval. The pre-determined time interval may include a number of days or a number of weeks.

In some embodiments, collecting the series of heartbeat waveforms and generating the heartbeat waveform space are repeated at future times to update the heartbeat waveform space to the most current representation of a cardiac status.

In some embodiments, the score includes a scalar function, with the scalar function including at least one of an energy and power of a PDD vector. In other embodiments, the score includes a vector function of the PDD vector.

In some embodiments, the method includes selecting an indication from a list of clinical indications after calculating the score. In certain embodiments, the clinical indication includes a warning message regarding an upcoming cardiac episode. In some embodiments, the clinical indication includes a measure of progression or regression of at least one cardiac pathology. In some embodiments, the cardiac pathology includes at least one chronic heart failure.

According to another example embodiment of the present disclosure, the steps of the method for monitoring cardiac pathology are stored on a non-transitory machine-readable medium comprising instructions, which when implemented by one or more processors perform the recited steps.

Other example embodiments of the disclosure and aspects will become apparent from the following description taken in conjunction with the following drawings.

BRIEF DESCRIPTION OF THE DRAWINGS

Embodiments are illustrated by way of example and not limitation in the figures of the accompanying drawings, in which like references indicate similar elements.

DETAILED DESCRIPTION

The following detailed description includes references to the accompanying drawings, which form a part of the detailed description. The drawings show illustrations in accordance with exemplary embodiments. These exemplary embodiments, which are also referred to herein as "examples," are described in enough detail to enable those skilled in the art to practice the present subject matter. The embodiments can be combined, other embodiments can be utilized, or structural, logical, and electrical changes can be made without departing from the scope of what is claimed. The following detailed description is, therefore, not to be taken in a limiting sense, and the scope is defined by the appended claims and their equivalents.

The present disclosure provides systems and methods for early detection of potentially life-threatening cardiac pathology. The systems can be implemented as stand-alone units for consumer use or embedded within medical devices such as ECG monitors and cardiac assistive devices like implantable pacemakers.

According to various example embodiments, a method for monitoring of cardiac pathology includes generating, based on the series of the heartbeat waveforms, a heartbeat waveform space. The method includes receiving a test heartbeat waveform. The method allows projecting the test heartbeat waveform on the heartbeat waveform space to obtain a projected heartbeat waveform. The method includes subtracting the projected heartbeat waveform from the test heartbeat waveform to obtain a PDD vector. The method allows calculating, based on the PDD vector, a score. The method includes providing, based on the score, a clinical indication associated with at least one cardiac pathology.

Figure 1:
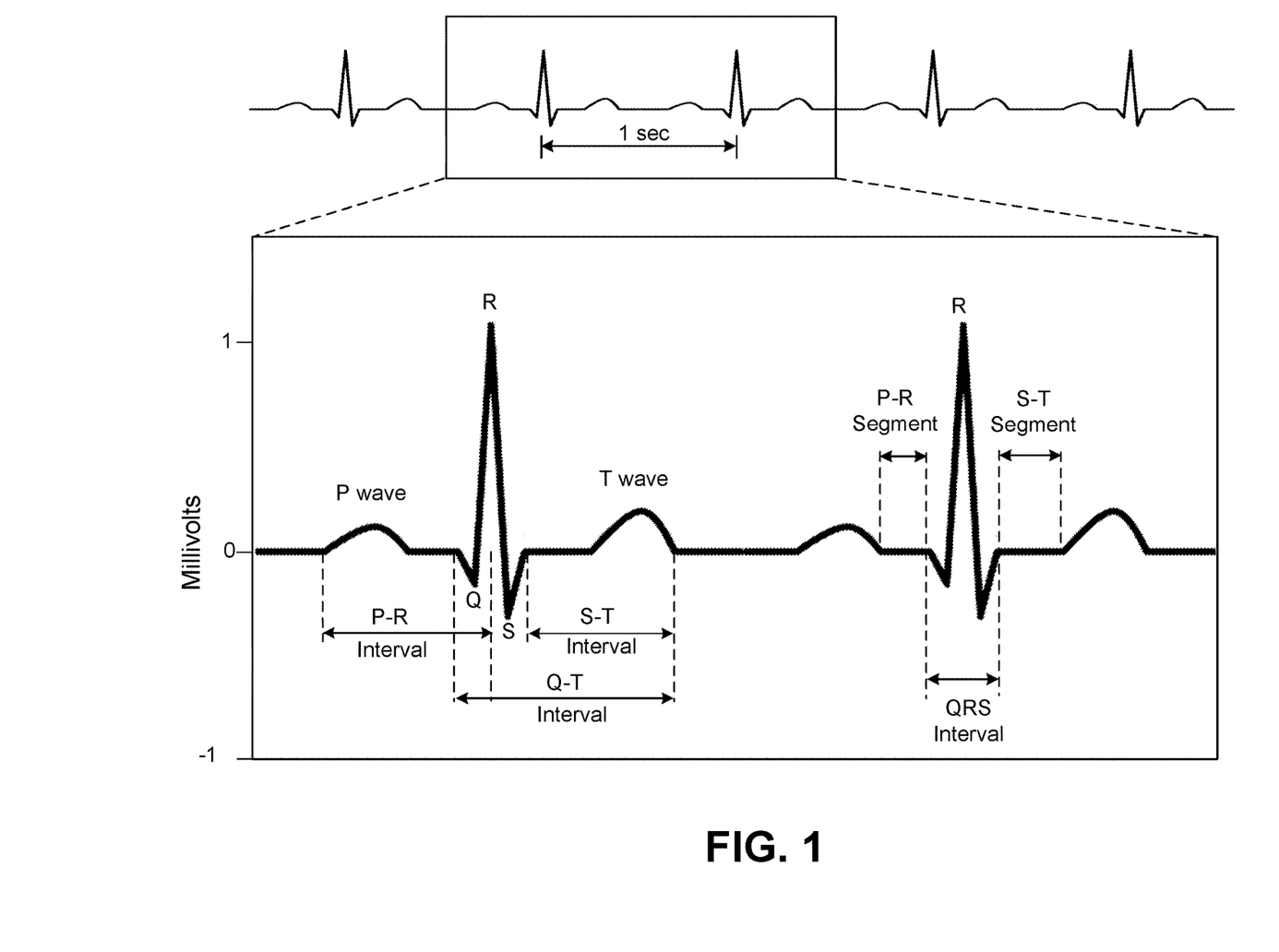
FIG. 1 illustrates an example ECG waveform.

FIG. 1 shows an example ECG waveform. Electrocardiography is a transthoracic interpretation of the electrical activity of the heart over a period of time, as detected by electrodes attached to the outer surface of the skin and recorded by a device external to the body.

The recording produced using a noninvasive procedure is termed ECG. An ECG is a test that records the electrical activity of the heart. It is used to measure the rate and regularity of heartbeats as well as the size and position of the chambers, the presence of any damage to the heart such as caused by MI, and the effects of drugs or devices used to regulate the heart such as pacemakers.

An ECG device detects and amplifies the tiny electrical changes on the skin that are caused when the heart muscle depolarizes during each heartbeat. At rest, each heart muscle cell has a negative charge across its outer wall. Increasing this negative charge towards zero is called depolarization, which activates the mechanisms in the cell that cause it to contract. During each heartbeat, a healthy heart will have an orderly progression of a wave of depolarization that is triggered by the cells in the sinoatrial node, spreads out through the atrium, passes through intrinsic conduction pathways, and then spreads all over the ventricles. This is detected as tiny rises and falls in the voltage between two electrodes placed on either side of the heart and is displayed as a wavy line either on a screen or on paper. This display indicates the overall rhythm of the heart and weaknesses in different parts of the heart muscle.

Usually more than two electrodes are used and they can be combined into a number of pairs. For example: Left arm (LA), right arm (RA) and left leg (LL) electrodes form the three pairs LA+RA, LA+LL, and RA+LL. The output from each pair is known as a lead. Each lead is said to look at the heart from a different angle. Different types of ECGs can be referred to by the number of leads that are recorded (for example 3-lead, 5-lead, or 12-lead ECGs).

A 12-lead ECG is one in which 12 different electrical signals are recorded at approximately the same time and is often used as a one-off recording of an ECG and traditionally printed out as a paper copy. The 3-lead and 5-lead ECGs tend to be monitored continuously and viewed only on the screen of an appropriate monitoring device, for example during an operation or while being transported in an ambulance.

An ECG is commonly used to measure and diagnose abnormal rhythms of the heart, particularly abnormal rhythms caused by damage to the conductive tissue that carries electrical signals or abnormal rhythms caused by electrolyte imbalances. In a MI, the ECG can indicate whether the heart muscle has been damaged in specific areas, although not all areas of the heart are covered. The ECG cannot reliably measure the pumping ability of the heart, for which ultrasound based tests can be used.

Typically, myocardial ischemia and MI give rise to notable changes in the ECG waveform: T waves become tall and upright before the ST elevation, the elevation of which is thought to be due to an opening of ATP-sensitive $K^+$ channels. However, ST elevation is not a highly specific marker. For example, the majority of healthy adult men have concave ST elevation of 0.1 mV or more in at least one precordial lead, and moreover, ST elevation can occur during pericarditis, hyperkalemia, and pulmonary embolism.

MI can also produce broad and deep negative deflections in the ECG known as Q waves, although their pathological substrate is unclear. Q waves remain permanently. The ST segment eventually returns to normal, while T waves may return to upright, as the infarcted area becomes electrically unexcitable and then necrotic before forming scar tissue. However, these changes are usually a result of severe cardiac pathology or extensive cardiovascular stress, and normally are not evident at the early pre-clinical stage.

Various embodiments of the present disclosure provide methods for defining, extracting, and analyzing subtle deflections in ECG waveforms. The subtle deflections are masked by clinical features of the ECG (P-QRS-T) waveform and normally go unnoticed. Once unmasked, analysis of the deflections can provide an early warning against upcoming or worsening of cardiac episodes, such that preventive measures can be taken to reduce the severity of such upcoming episodes.

Early warning against upcoming or worsening of cardiac episodes can be beneficially implemented in a wide range of devices, ranging from consumer spot-check devices for home use, to ambulatory medical equipment such as ECG monitors, and all the way to implantable cardiac assistive devices such as implantable pacemakers.

The ECG is an easy and helpful test for assessment of the heart's function and possible underlying problems. However, the sensitivity and specificity of an ECG analysis is limited. A limitation pertaining to methods of the current disclosure is that a normal ECG does not rule out heart disease or even an evolving MI, and additional tests are often recommended. In addition, the results of an ECG examination are often non-specific, meaning that abnormal findings do not necessarily refer to one condition but could be the result of multiple problems.

For example, in a stress test, the patient can be asked to exercise while the electrical activity of the heart is monitored for the purpose of establishing whether there might be any limitations to the heart's function or the patient's exercise tolerance. If a patient is unable to exercise, or concomitant investigations like an ECG or MRI are to be done simultaneously, specific drugs stimulating the heartbeat can be given instead to simulate a strenuous activity.

Figure 2:
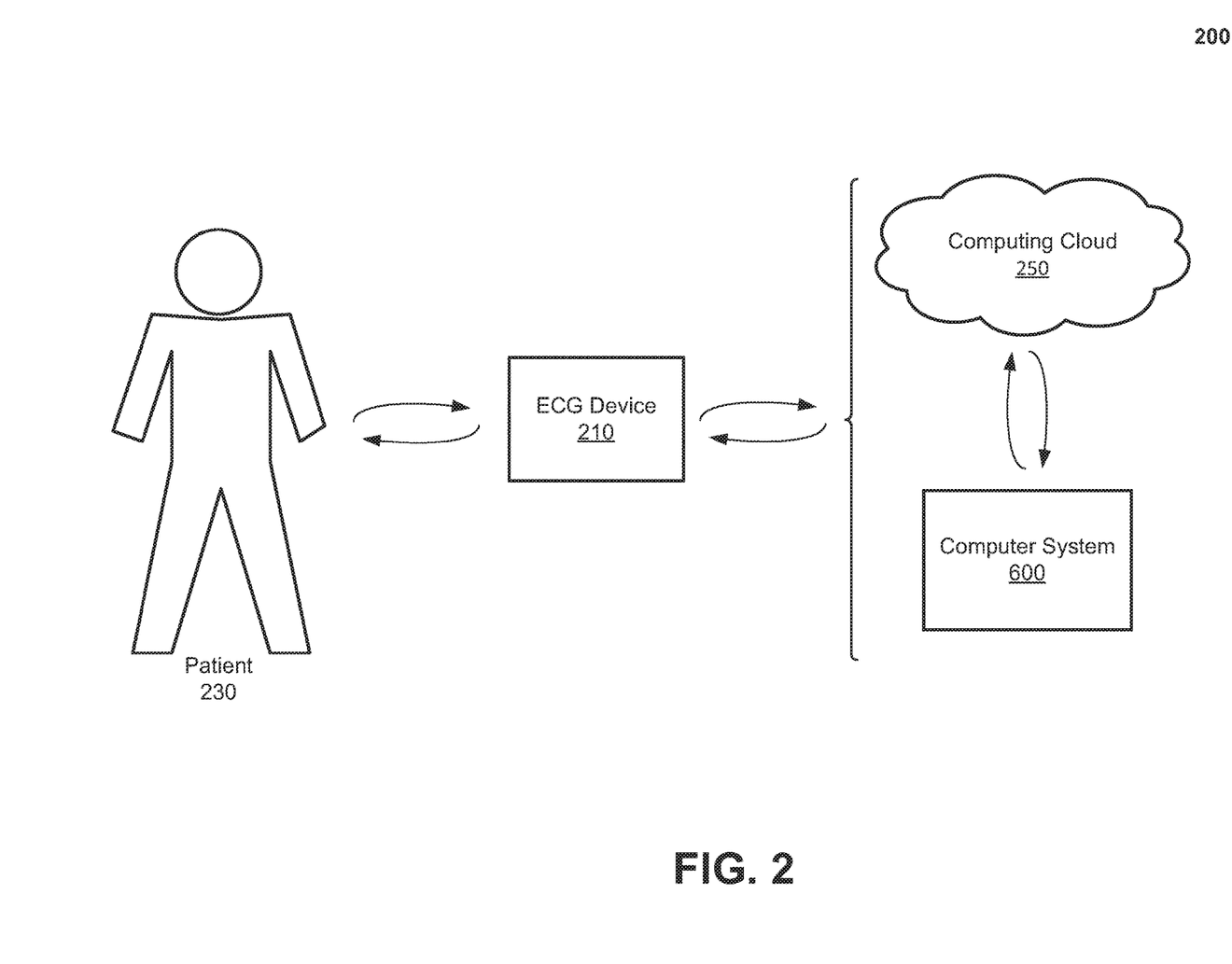
FIG. 2 is a block diagram showing an example environment wherein method of monitoring cardiac pathology can be implemented.

FIG. 2 shows an example environment 200 wherein a method for the prediction and monitoring of cardiac pathology can be practiced. The environment 200 includes at least an ECG device 210. The ECG device 210 is operable to record ECG data of patient 230. In various embodiments, ECG device 210 includes a stationary hospital ECG system, a portable ECG system, a personal wearable ECG device, and any other devices or systems that provide ECG measurements. In some embodiments, the wearable ECG device is worn by a patient 230, for example on a wrist, for an extended period of time during everyday life. The wearable ECG device can be carried out as a watch, a bracelet, a wristband, and the like. In various embodiments, ECG data are collected for an extended period of time (for example, weeks, month, and years). In some embodiments, the ECG data are taken periodically (for example, once a day, a week, or a month). In other embodiments, when a patient wears a wearable ECG device, the ECG data are taken constantly.

In some embodiments, ECG data are provided for an analysis, for example to a computer system 600. In some embodiments, ECG data are provided to a cloud-based computing resource (also referred to as a computing cloud 250). In some embodiments, the computing cloud 250 includes one or more server farms/clusters comprising a collection of computer servers and is co-located with network switches and/or routers. In various embodiments, the computing cloud 250 is operable to store historical data concerning patient health status including ECG data and medical parameters collected over days, weeks, months, and years. The computing cloud 250 can be operable to run one or more applications and to provide reports regarding health status of the patient.

Figure 3:
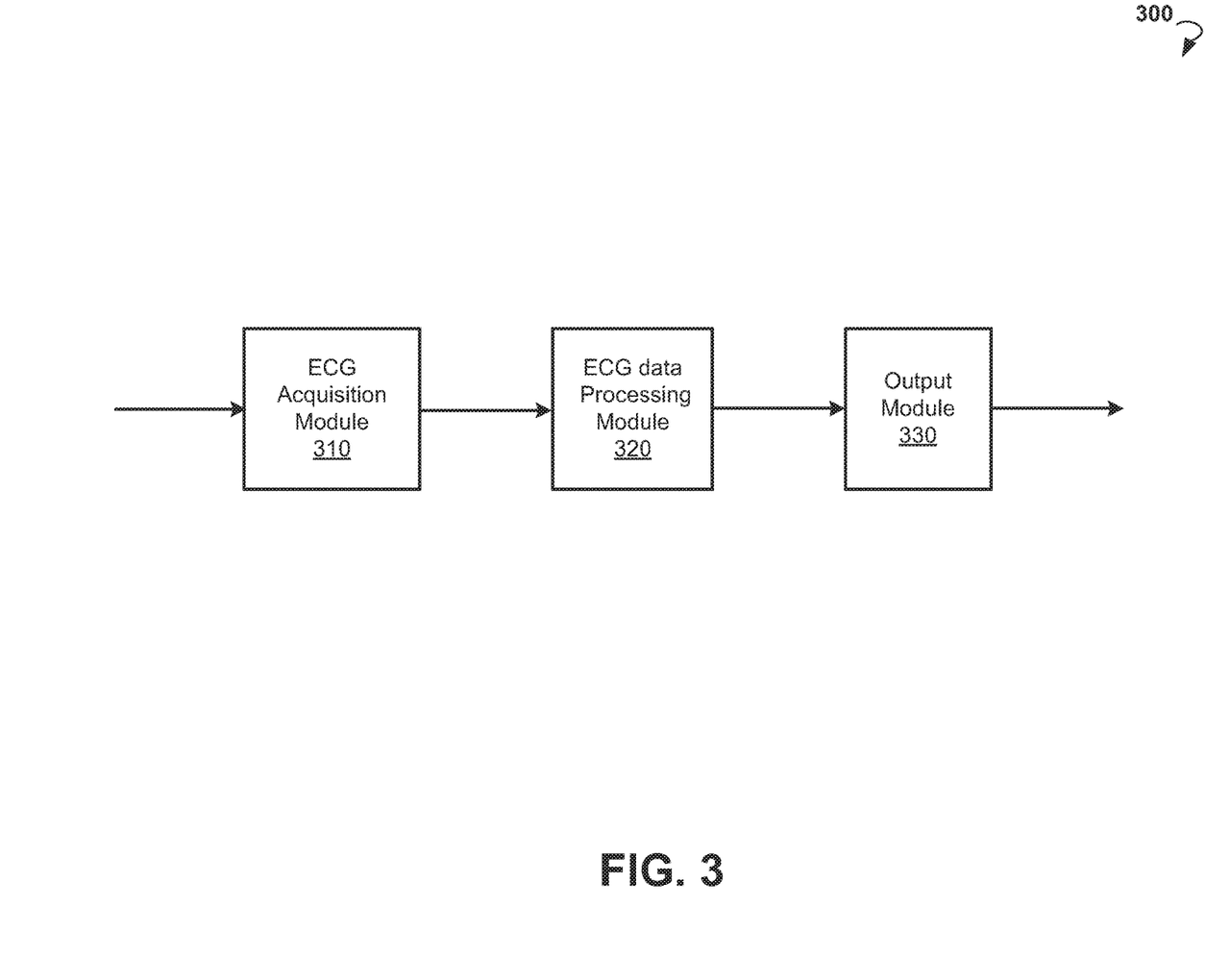
FIG. 3 is a block diagram showing an example system for ECG data processing.

FIG. 3 is a block diagram showing components of system 300 for processing ECG data, according to some example embodiments. The system 300 can include an ECG acquisition module 310, an ECG data processing module 320, and an output module 330. In some embodiments, the modules 310-330 can be stored as instructions in memory of the computer system 600 or computing cloud 250, and executed by a processor. In some embodiments, the system 300 can be embedded within a mobile device such as cellphone/smartphone or laptop/notebook/tablet computer.

In some embodiments, the ECG acquisition module 310 is configured to receive and digitalize the ECG data. The ECG acquisition module 310 can include one or more analog-to-digital converters to transform the electrical signals from electrical sensors to digits.

In some embodiments, the ECG data processing module 320 is configured to analyze the ECG data to obtain medical parameters associated with cardiac pathologies and analyze trends in ECG parameters to track progression or remission of the cardiac pathologies.

In certain embodiments, a system incorporating ECG acquisition, ECG data processing module, and an output module such as a liquid crystal display (LCD) display can be embedded within a consumer device for personal use. For example, the system 300 can be embedded within a thin and flexible powered card that includes a touch ECG sensor, a computing Application-Specific Integrated Circuit (ASIC), and a display. The card may also include a standard or wireless communication interface.

In some embodiments, the output module 330 is configured to provide reports and alert messages regarding a health status of the patient.

Figure 4:
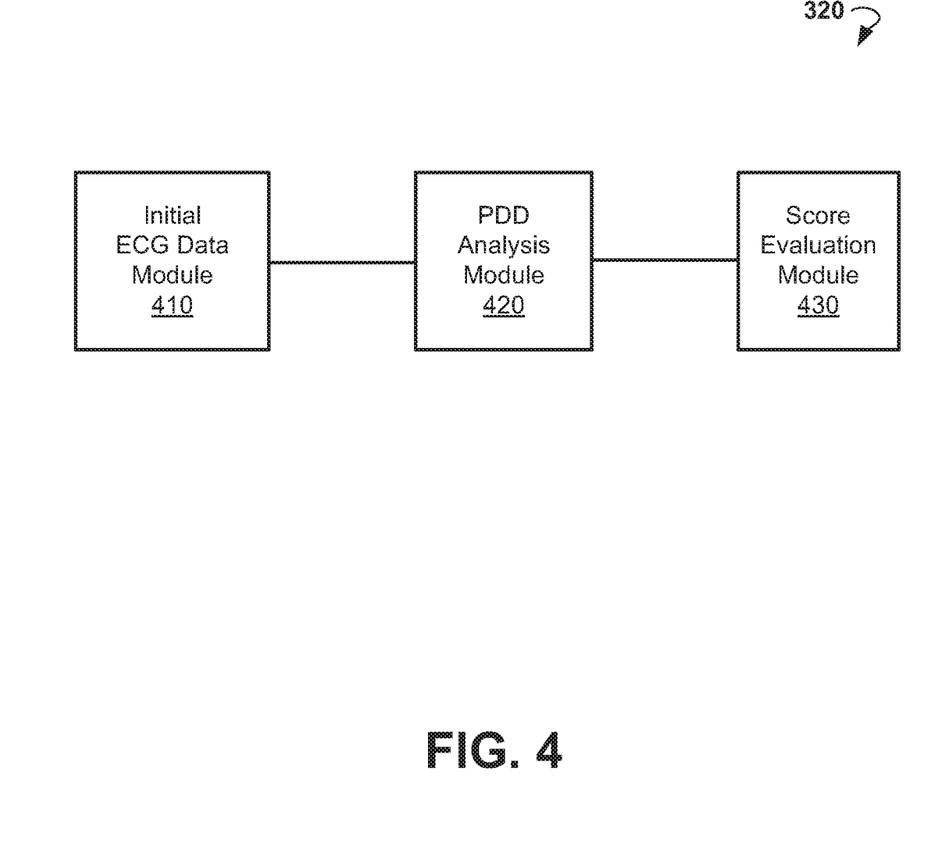
FIG. 4 is a block diagram showing a system for monitoring of cardiac pathology.

FIG. 4 shows components of ECG data processing module 320 suitable for implementing methods of the present disclosure. The ECG data processing module 320 may include an initial ECG data module 410, a PDD analysis module 420, and a score evaluation module 430.

In some embodiments, initial ECG data module 410 is operable to generate a model of a heartbeat waveform space. In some embodiments, a series of ECG heartbeat waveforms is collected and analyzed to create a model of the heartbeat waveform space of an individual. In certain embodiments, a principal component analysis is used for the analysis of the heartbeat waveforms. In certain embodiments, an initial series of ECG heartbeat waveforms is collected over a time interval of several days or weeks. The initial series of ECG heartbeat waveforms can be analyzed to create a model of an individual's pre-existing heartbeat waveform space. In other embodiments, the initial series of ECG heartbeat waveforms is updated periodically to capture and follow the most current state of the individual's cardiac function. The updated series of ECG heartbeat waveforms is then analyzed to create the model of the individual's pre-existing heartbeat waveform space.

In some embodiments, the series of ECG heartbeat waveforms is collected from a healthy individual and subsequently used to monitor the individual's health status. In certain embodiments, the series of ECG heartbeat waveforms is collected from a heart patient and subsequently used to monitor the heart patient's health status.

In various embodiments, a PDD analysis module is operable to receive a test ECG heartbeat waveform and perform a PDD analysis. In various embodiments, a PDD analysis is performed to detect small deviations of the test ECG heartbeat from the model of the heartbeat waveform space determined in initial ECG data module 410.

The PDD are masked by large ECG heartbeat waveform components (P-QRS-T). The PDD are reflective of preclinical stages of abnormal cardiac function, are specific to clinical progression of cardiac deterioration, and can be detected during normal heart function without a need for strenuous activity. In various embodiments, PDD are determined and unmasked using a statistical signal processing.

In some embodiments, PDD analysis can be incorporated within or as an add-on to existing ECG monitoring devices. In certain embodiments, PDD analysis can be incorporated within or as an add-on to existing cardiac assistive or monitoring devices, such as implantable cardiac pacemakers, where indications and warnings can be transmitted via the embedding device's communication channel.

In some embodiments, a test ECG heartbeat waveform is captured and then projected onto the modeled heartbeat waveform space. In some embodiments, PDD are extracted by subtraction of the test waveform projection from the original test heartbeat waveform.

In certain embodiments, a scalar magnitude (also referred to as a score) of PDD is calculated in score evaluation module 430. In some embodiments, the score of PDD is calculated using energy or power analysis. The score is then compared to a pre-determined threshold. If the score is greater than the threshold, then a warning message is provided. In other embodiments, an appropriate warning message is selected from a list of warning messages based on score magnitude.

In other embodiments, a score vector of PDD magnitudes is defined such that each element of the vector of PDD magnitudes relates to a specific temporal bin within the test and projected heartbeat waveforms. The score vector of PDD magnitudes is compared to a vector of pre-determined thresholds. An appropriate warning is selected from a list of warnings based on PDD magnitudes that exceed their respective thresholds.

In some other embodiments, a score vector of PDD magnitudes is defined such that each element of the vector of PDD magnitudes relates to a specific temporal bin within the test and projected heartbeat waveforms. A transformation (for example, weighted average) is used to transform the score vector of PDD magnitudes into a scalar score. If the scalar score is greater than a pre-determined threshold, then a warning message is provided. In other embodiments, an appropriate warning message is selected from a list of warnings based on the magnitude of the score.

In some embodiments, a series of ECG heartbeat waveforms is collected from a plurality of healthy individuals. The series of ECG heartbeat waveforms is analyzed to create an approximate model for a healthy heartbeat waveform space of the population at large.

In some embodiments, PDD are extracted by subtraction of the test heartbeat waveform projection onto a healthy heartbeat waveform space from the original test heartbeat waveform.

In some embodiments, a lookup table is used to provide a relationship between different cardiac pathologies and respective temporal bins of heartbeat waveforms. In certain embodiments, a combination of standard ECG analysis and PDD analysis is used to provide cardiac diagnostics.

In further embodiments, trends in PDD and scores of PDD are tracked for a particular individual over time. Based on the dynamics of changes of PDD scores, a determination of a worsening of cardiac function can be made. For example, if one of the PDD scores keeps approaching a pre-determined threshold, then an early warning for potential heart failure can be provided to the individual.

Figure 5:
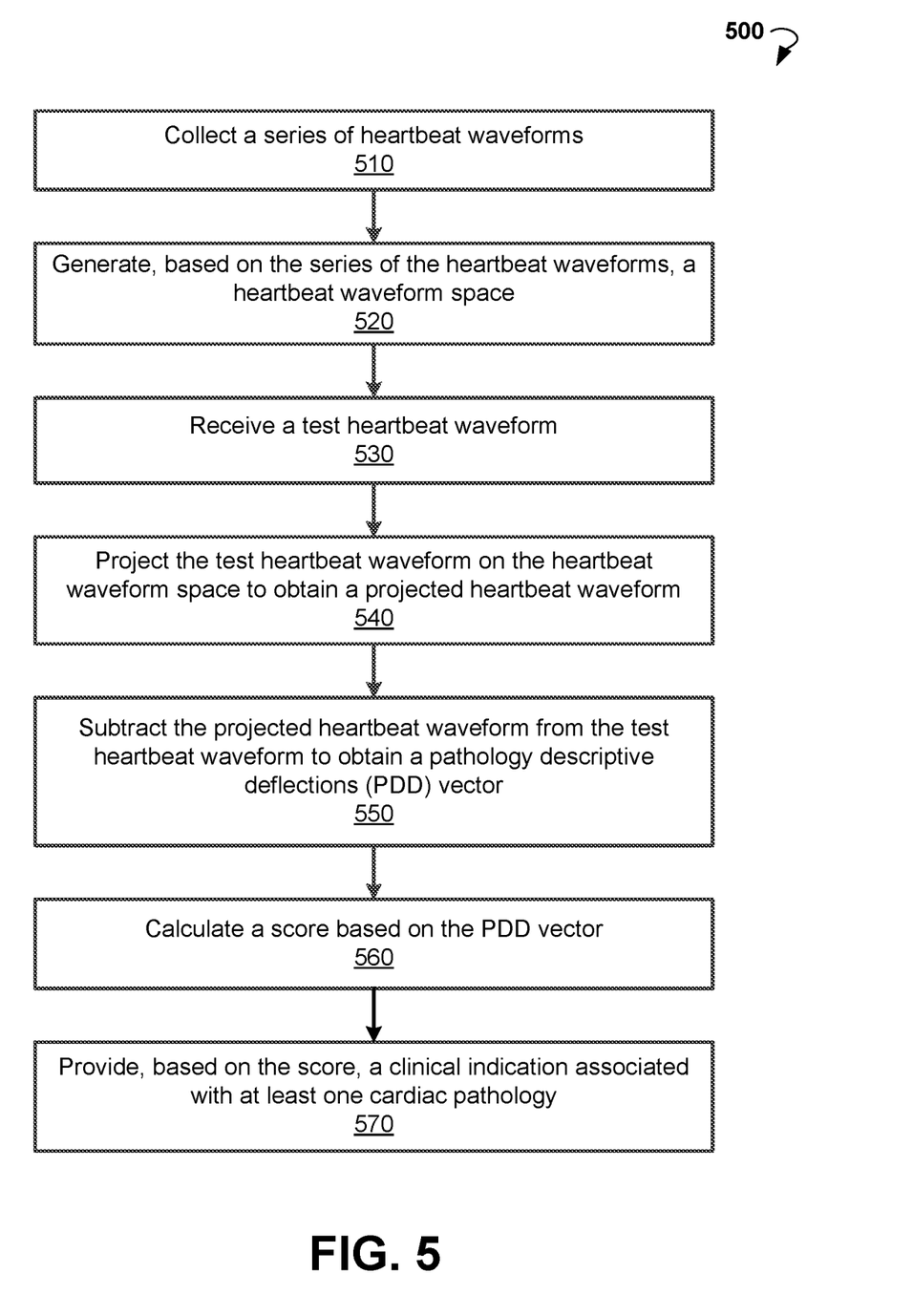
FIG. 5 is a flow chart showing steps of an example method for monitoring of cardiac pathology.

FIG. 5 is a flow chart showing an example method 500 for monitoring cardiac pathology, according to an example embodiment. The method 500 can commence with collecting a series of heartbeat waveforms, at block 510. The series can be collected during several days or weeks. In some embodiments, the series is collected from art individual. In other embodiments, the series is collected from a plurality of healthy individuals.

In block 520, method 500 can generate, based on the series of the heartbeat waveforms, a heartbeat waveform space.

In block 530, a test heartbeat waveform is received. In block 540, the method 500 includes projecting the test heartbeat waveform onto the heartbeat waveform space to obtain a projected heartbeat waveform. In block 550, the projected heartbeat waveform is subtracted from the test heartbeat waveform to obtain a PDD vector.

In block 560, method 500 proceeds with calculating a score based on the PDD vector. In block 570, method 500 allows providing, based on the score, a clinical indication associated with at least one cardiac pathology. The cardiac pathology may include a chronic heart failure.

Figure 6:
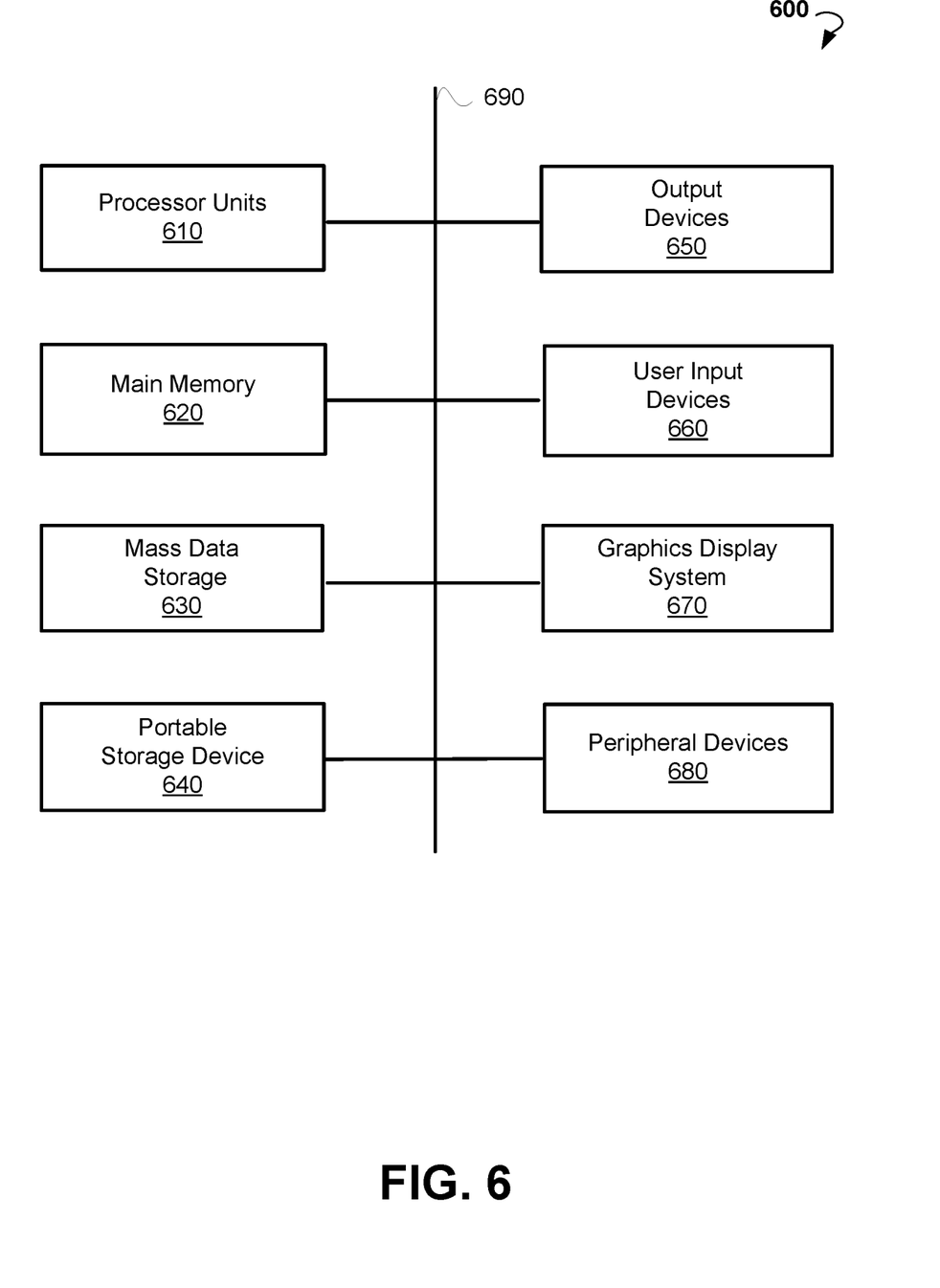
FIG. 6 shows a diagrammatic representation of a computing device for a machine, within which a set of instructions for causing the machine to perform any one or more of the methodologies discussed herein can be executed.

FIG. 6 illustrates a computer system 600 that may be used to implement embodiments of the present disclosure, according to an example embodiment. The computer system 600 may serve as a computing device for a machine, within which a set of instructions for causing the machine to perform any one or more of the methodologies discussed herein can be executed. The computer system 600 can be implemented in the contexts of the likes of computing systems, networks, servers, or combinations thereof. The computer system 600 includes one or more processor units 610 and main memory 620. Main memory 620 stores, in part, instructions and data for execution by processor units 610. Main memory 620 stores the executable code when in operation. The computer system 600 further includes a mass data storage 630, a portable storage device 640, output devices 650, user input devices 660, a graphics display system 670, and peripheral devices 680. The methods may be implemented in software that is cloud-based.

The components shown in FIG. 6 are depicted as being connected via a single bus 690. The components may be connected through one or more data transport means. Processor units 610 and main memory 620 are connected via a local microprocessor bus, and mass data storage 630, peripheral devices 680, the portable storage device 640, and graphics display system 670 are connected via one or more I/O buses.

Mass data storage 630, which can be implemented with a magnetic disk drive, solid state drive, or an optical disk drive, is a non-volatile storage device for storing data and instructions for use by processor units 610. Mass data storage 630 stores the system software for implementing embodiments of the present disclosure for purposes of loading that software into main memory 620.

The portable storage device 640 operates in conjunction with a portable non-volatile storage medium, such as a floppy disk, compact disk, Digital Versatile Disc (DVD), or USB storage device, to input and output data and code to and from the computer system 600. The system software for implementing embodiments of the present disclosure is stored on such a portable medium and input to the computer system 600 via the portable storage device 640.

User input devices 660 provide a portion of a user interface. User input devices 660 include one or more microphones; an alphanumeric keypad, such as a keyboard, for inputting alphanumeric and other information; or a pointing device, such as a mouse, trackball, stylus, or cursor direction keys. User input devices 660 can also include a touchscreen. Additionally, the computer system 600 includes output devices 650. Output devices 650 include speakers, printers, network interfaces, and monitors.

Graphics display system 670 includes a LCD or other suitable display device. Graphics display system 670 receives textual and graphical information and processes the information for output to the display device. Peripheral devices 680 may include any type of computer support device to add additional functionality to the computer system.

The components provided in the computer system 600 of FIG. 6 are those typically found in computer systems that may be suitable for use with embodiments of the present disclosure and are intended to represent a broad category of such computer components that are well known in the art. Thus, the computer system 600 can be a personal computer, handheld computing system, telephone, mobile computing system, workstation, tablet, phablet, mobile phone, server, minicomputer, mainframe computer, or any other computing system. The computer may also include different bus configurations, networked platforms, multi-processor platforms, and the like. Various operating systems may be used including UNIX, LINUX, WINDOWS, MAC OS, PALM OS, ANDROID, IOS, QNX, TIZEN, and other suitable operating systems.

It is noteworthy that any hardware platform suitable for performing the processing described herein is suitable for use with the embodiments provided herein. Computer-readable storage media refer to any medium or media that participate in providing instructions to a central processing unit, a processor, a microcontroller, or the like. Such media may take forms including, but not limited to, non-volatile and volatile media such as optical or magnetic disks and dynamic memory, respectively. Common forms of computer-readable storage media include a floppy disk, a flexible disk, a hard disk, magnetic tape, any other magnetic storage medium, a Compact Disk Read Only Memory disk, DVD, Blu-ray disc, any other optical storage medium, RAM, Programmable Read-Only Memory, Erasable Programmable Read-Only Memory, Electronically Erasable Programmable Read-Only Memory, flash memory, and/or any other memory chip, module, or cartridge.

In some embodiments, the computer system 600 may be implemented as a cloud-based computing environment, such as a virtual machine operating within a computing cloud. In other embodiments, the computer system 600 may itself include a cloud-based computing environment, where the functionalities of the computer system 600 are executed in a distributed fashion. Thus, the computer system 600, when configured as a computing cloud, may include pluralities of computing devices in various forms, as will be described in greater detail below.

In general, a cloud-based computing environment is a resource that typically combines the computational power of a large grouping of processors (such as within web servers) and/or that combines the storage capacity of a large grouping of computer memories or storage devices. Systems that provide cloud-based resources may be utilized exclusively by their owners or such systems may be accessible to outside users who deploy applications within the computing infrastructure to obtain the benefit of large computational or storage resources.

The cloud may be formed, for example, by a network of web servers that comprise a plurality of computing devices, such as the computer system 600, with each server (or at least a plurality thereof) providing processor and/or storage resources. These servers may manage workloads provided by multiple users (e.g., cloud resource customers or other users). Typically, each user places workload demands upon the cloud that vary in real-time, sometimes dramatically. The nature and extent of these variations typically depends on the type of business associated with the user.

Figure 7:
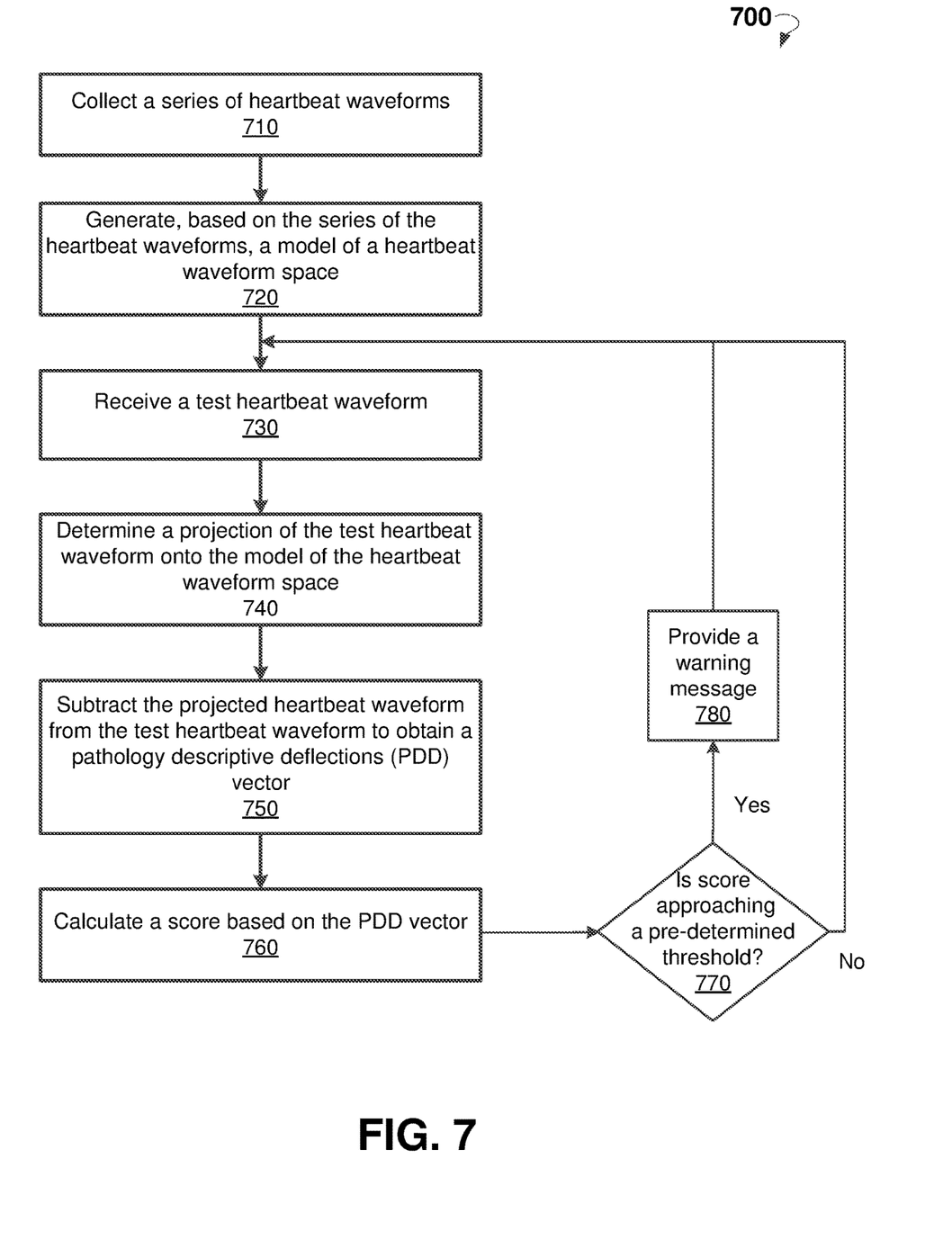
FIG. 7 is a flow chart showing steps of an example method for monitoring of cardiac pathology.

FIG. 7 is a flow chart showing a method 700 for monitoring cardiac pathology, according to an example embodiment. The method 700 may commence, in block 710, with collecting, by a processor, a series of heartbeat waveforms. The series of heartbeat waveforms are recorded by an electrocardiogram (ECG) device during a pre-determined time interval.

In block 720, the method 700 can commence with performing, by the processor, a principal component analysis on the series of the heartbeat waveforms to generate a model of a heartbeat waveform space. The method 700 may further include periodically performing operations, in blocks 730-780.

In block 730, the method 700 may proceed with receiving, by the processor, a test heartbeat waveform of an individual. The test heartbeat waveform can be recorded by the ECG device.

In block 740, the method 700 may proceed with determining, by the processor, a projection of the test heartbeat waveform onto the model of the heartbeat waveform space.

In block 750, the method can proceed with subtracting, by the processor, the projection of the test heartbeat waveform from the test heartbeat waveform to obtain a PDD vector. The PDD vector includes magnitudes of deviations of the test heartbeat waveform from the model of a heartbeat waveform space. The magnitudes relate to corresponding temporal bins within the test heartbeat waveform, with the temporal bins relating to cardiac pathologies. The PDD vector is reflective of pre-clinical stages of an abnormal cardiac function.

In block 760, the method 700 may proceed with calculating, by a processor, a score based on the magnitudes.

In block 770, the method 700 may proceed with determining, by the processor, that the score keeps approaching a pre-determined threshold. For examples, the determination that the score keeps approaching the pre-determined threshold may include inspecting values of the score calculated in a predetermined number of preceding iterations of operations in blocks 730-760 and determining that the values of the score are approaching the pre-determined threshold.

In block 780, the method 700 may proceed with providing, by the processor, a warning message concerning the at least one cardiac pathology to the individual if the score keeps approaching the predetermined threshold.

Thus, methods and systems for monitoring of cardiac pathology have been described. Although embodiments have been described with reference to specific example embodiments, it will be evident that various modifications and changes can be made to these example embodiments without departing from the broader spirit and scope of the present application. Accordingly, the specification and drawings are to be regarded in an illustrative rather than a restrictive sense.

What is claimed is:

1. A method for monitoring cardiac pathology, the method comprising:
   collecting, by a processor, a series of heartbeat waveforms, the series of heartbeat waveforms being recorded by an electrocardiogram (ECG) device during a pre-determined time interval;
   performing, by the processor, a principal component analysis on the series of the heartbeat waveforms to generate a model of a heartbeat waveform space;
   periodically:
      receiving, by the processor, a test heartbeat waveform of an individual, the test heartbeat waveform being recorded by the ECG device;
      determining, by the processor, a projection of the test heartbeat waveform onto the model of the heartbeat waveform space;
      subtracting, by the processor, the projection of the test heartbeat waveform from the test heartbeat waveform to obtain a pathology descriptive deflections (PDD) vector, wherein the PDD vector includes magnitudes of deviations of the test heartbeat waveform from the model of the heartbeat waveform space, wherein each of the magnitudes relates to a temporal bin of temporal bins within the test heartbeat waveform, the temporal bins being related to at least one cardiac pathology, the PDD vector being reflective of pre-clinical stages of an abnormal cardiac function; and
      calculating, by a processor and based on the magnitudes, a score;
   determining, by the processor, that the score is approaching a pre-determined threshold; and
   based on the determination, providing, by the processor, a warning message concerning the at least one cardiac pathology to the individual.

2. The method of claim 1, wherein the series of the heartbeat waveforms is collected from the individual.

3. The method of claim 1, wherein the series of the heartbeat waveforms is collected from a plurality of healthy individuals.

4. The method of claim 1, wherein the pre-determined time interval includes at least one of a number of days or a number of weeks.

5. The method of claim 1, further comprising repeating, by the processor, the collecting the series of heartbeat waveforms and performing the principal component analysis on the series of heartbeat waveforms to generate the model of the heartbeat waveform space at future times to update the heartbeat waveform space to a most current representation of a cardiac status.

6. The method of claim 1, wherein the score includes a scalar function, the scalar function including at least one of an energy and power of the PDD vector.

7. The method of claim 1, wherein the score includes a vector function of the PDD vector.

8. The method of claim 1, further comprising, after calculating the score, selecting, by the processor and based on a magnitude of the score, the warning message from a list of warnings.

9. The method of claim 1, wherein the warning message includes a measure of progression or regression of the at least one cardiac pathology.

10. The method of claim 1, wherein the at least one cardiac pathology includes chronic heart failure.

11. A system for monitoring cardiac pathology, the system comprising:
 a processor; and
 a memory communicatively coupled with the processor, the memory storing instructions which, when executed by the processor, perform a method comprising:
  collecting a series of heartbeat waveforms, the series of heartbeat waveforms being recorded by an electrocardiogram (ECG) device during a pre-determined time interval;
  performing a principal component analysis on the series of the heartbeat waveforms to generate a model of a heartbeat waveform space;
  periodically:
   receiving a test heartbeat waveform of an individual, the test heartbeat waveform being recorded by the ECG device;
   determining a projection of the test heartbeat waveform onto the model of the heartbeat waveform space;
   subtracting the projection of the test heartbeat waveform from the test heartbeat waveform to obtain a pathology descriptive deflections (PDD) vector, wherein the PDD vector includes magnitudes of deviations of the test heartbeat waveform from the model of the heartbeat waveform space, wherein each of the magnitudes relates to a temporal bin of temporal bins within the test heartbeat waveform, the temporal bins being related to at least one cardiac pathology, the PDD vector being reflective of pre-clinical stages of an abnormal cardiac function; and
   calculating, based on the magnitudes, a score;
  determining that the score is approaching a pre-determined threshold; and
  based on the determination, providing a warning message concerning the at least one cardiac pathology to the individual.

12. The system of claim 11, wherein the series of the heartbeat waveforms is collected from the individual.

13. The system of claim 11, wherein the series of the heartbeat waveforms is collected from a plurality of healthy individuals.

14. The system of claim 11, wherein the pre-determined time interval includes at least one of a number of days or a number of weeks.

15. The system of claim 11, further comprising repeating the collecting the series of heartbeat waveforms and performing the principal component analysis on the series of heartbeat waveforms to generate the model of the heartbeat waveform space at future times to update the heartbeat waveform space to a most current representation of a cardiac status.

16. The system of claim 11, wherein the score includes a scalar function, the scalar function including at least one of an energy and power of the PDD vector.

17. The system of claim 11, wherein the score includes a vector function of the PDD vector.

18. The system of claim 11, further comprising, after calculating the score, selecting, based on magnitude of the score, the warning message from a list of warnings.

19. The system of claim 11, wherein the warning message includes a measure of progression or regression of the at least one cardiac pathology.

20. The system of claim 11, wherein the at least one cardiac pathology includes chronic heart failure.

21. A non-transitory computer-readable storage medium having embodied thereon instructions, which when executed by a processor, perform steps of a method, the method comprising:
 collecting a series of heartbeat waveforms, the series of heartbeat waveforms being recorded by an electrocardiogram (ECG) device during a pre-determined time interval;
 performing a principal component analysis on the series of the heartbeat waveforms to generate a model of a heartbeat waveform space;
 periodically:
  receiving a test heartbeat waveform of an individual, the test heartbeat waveform being recorded by the ECG device;
  determining a projection of the test heartbeat waveform onto the model of the heartbeat waveform space;
  subtracting the projection of the heartbeat waveform from the test heartbeat waveform to obtain a pathology descriptive deflections (PDD) vector, wherein the PDD vector includes magnitudes of deviations of the test heartbeat waveform from the model of the heartbeat waveform space, wherein each of the magnitudes relates to a temporal bin of temporal bins within the test heartbeat waveform, the temporal bins being related to at least one cardiac pathology, the PDD being reflective of pre-clinical stages of an abnormal cardiac function; and
  calculating, based on the magnitudes, a score;
 determining that the score is approaching a pre-determined threshold; and
 based on the determination, providing a warning message concerning the at least one cardiac pathology to the individual.

* * * * *